(12) United States Patent
Kadow et al.

(10) Patent No.: US 7,183,284 B2
(45) Date of Patent: Feb. 27, 2007

(54) AMINIUM SALTS OF 1,2,3-TRIAZOLES AS PRODRUGS OF DRUGS INCLUDING ANTIVIRAL AGENTS

(75) Inventors: John F. Kadow, Wallingford, CT (US); Alicia Regueiro-Ren, Middletown, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/301,046

(22) Filed: Dec. 12, 2005

(65) Prior Publication Data

US 2006/0142298 A1   Jun. 29, 2006

Related U.S. Application Data

(60) Provisional application No. 60/640,185, filed on Dec. 29, 2004.

(51) Int. Cl.
| | | |
|---|---|---|
| *C07D 403/14* | (2006.01) | |
| *A61K 31/497* | (2006.01) | |
| *A61P 31/18* | (2006.01) | |
| *C07D 471/04* | (2006.01) | |

(52) U.S. Cl. .................. 514/252.12; 544/362; 546/113
(58) Field of Classification Search ........... 514/252.12; 544/361, 362
See application file for complete search history.

(56) References Cited

U.S. PATENT DOCUMENTS

| | | | |
|---|---|---|---|
| 6,469,006 | B1 | 10/2002 | Blair et al. |
| 6,476,034 | B2 | 11/2002 | Wang et al. |
| 2002/0061892 | A1 | 5/2002 | Wang et al. |
| 2003/0069245 | A1 | 4/2003 | Wallace et al. |
| 2003/0069266 | A1 | 4/2003 | Wang et al. |
| 2003/0207910 | A1 | 11/2003 | Wang et al. |
| 2004/0110785 | A1 | 6/2004 | Wang et al. |

FOREIGN PATENT DOCUMENTS

| | | |
|---|---|---|
| EP | 0242134 A | 10/1987 |
| WO | WO 92/00981 A1 | 1/1992 |
| WO | WO 00/76521 A | 12/2000 |
| WO | WO 01/62255 A | 8/2001 |
| WO | WO 02/085301 A2 | 10/2002 |
| WO | WO 03/068221 A1 | 8/2003 |
| WO | WO 03/082881 A | 10/2003 |
| WO | WO 03/092695 A1 | 11/2003 |
| WO | WO 04/000210 A2 | 12/2003 |

(Continued)

OTHER PUBLICATIONS

Stella, V.J., et al, Pharmacokinetics of Drug Targeting: Specific Implications for Targeting Via Prodrugs, Handbook of Experimental Pharmacology, Chapter 4, pp. 71-103, 1991.

Stella, V.J., et al, "Prodrugs. Do They Have Advantages in Clinical Practice?," DRUGS, 29(5), pp. 455-473, 1985.

(Continued)

*Primary Examiner*—Mark Berch
*Assistant Examiner*—Susanna Moore
(74) *Attorney, Agent, or Firm*—Jennifer Chin Chapman

(57) ABSTRACT

This disclosure provides compounds having drug and bio-affecting properties, their pharmaceutical compositions and method of use. In particular, the disclosure is concerned with new aminium salts of 1,2,3-triazoles which can be used as prodrugs to improve the solubility or pharmaceutical properties of 1,2,3-triazole containing compounds. More particularly, the present disclosure relates to compounds containing N-aminium-1,2,3-triazoles that are useful as antiviral agents and specifically for the treatment of HIV and AIDS.

7 Claims, 1 Drawing Sheet

In vivo data: Oral AUC in Rats vs. Dose Plots
(all doses are parent compound IV-a equivalent)

OTHER PUBLICATIONS

Stella, V.J., "Trends in Prodrug Research," Pharmacy International, 5(11), pp. 276-279, 1984.

Heimbach, T., et al, "Absorption Rate Limit Considerations for Oral Phosphate Prodrugs," Pharmaceutical Research, 20(6), pp. 848-856, 2003.

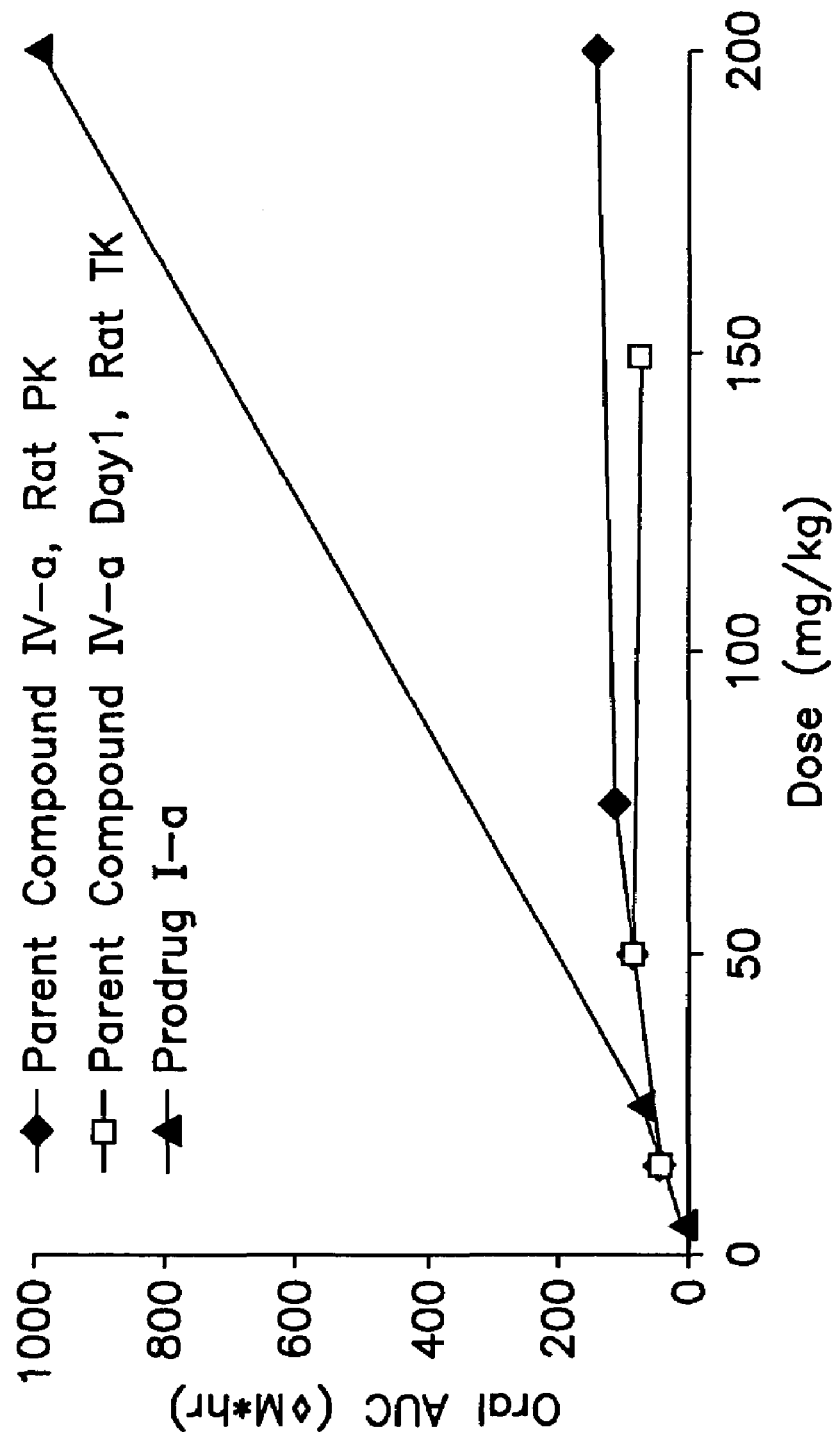

AMINIUM SALTS OF 1,2,3-TRIAZOLES AS PRODRUGS OF DRUGS INCLUDING ANTIVIRAL AGENTS

CROSS-REFERENCE TO RELATED APPLICATIONS

This application claims the benefit of U.S. Provisional Application Ser. No. 60/640,185 filed Dec. 29, 2004.

FIELD OF THE INVENTION

This invention provides compounds having drug and bio-affecting properties, their pharmaceutical compositions and method of use. In particular, the invention is concerned with new aminium salts of 1,2,3-triazoles which can be used as prodrugs to improve the solubility or pharmaceutical properties of 1,2,3-triazole containing compounds. More particularly, the present invention relates to compounds containing N-aminium-1,2,3-triazoles that are useful as antiviral agents and specifically for the treatment of HIV and AIDS.

BACKGROUND ART

HIV-1 (human immunodeficiency virus-1) infection remains a major medical problem, with an estimated 42 million people infected worldwide at the end of 2002. The number of cases of HIV and AIDS (acquired immunodeficiency syndrome) has risen rapidly. In 2002, ~5.0 million new infections were reported, and 3.1 million people died from AIDS. Currently available drugs for the treatment of HIV include ten nucleoside reverse transcriptase (RT) inhibitors or approved single pill combinations (zidovudine or AZT (or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), Combivir® (contains -3TC plus AZT), Trizivir® (contains abacavir, lamivudine, and zidovudine) and Emtriva® (emtricitabine); three non-nucleoside reverse transcriptase inhibitors: nevirapine (or Viramune®), delavirdine (or Rescriptor®) and efavirenz (or Sustiva®), nine peptidomimetic protease inhibitors or approved formulations: saquinavir, indinavir, ritonavir, nelfinavir, amprenavir, lopinavir, Kaletra® (lopinavir and Ritonavir), Atazanavir (Reyataz®), Fosamprenavir® and one fusion inhibitor which targets viral gp41 T-20 (FUZEON®). Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options.

Currently marketed HIV-1 drugs are dominated by either nucleoside reverse transcriptase inhibitors or peptidomimetic protease inhibitors. Non-nucleoside reverse transcriptase inhibitors (NNRTIs) have recently gained an increasingly important role in the therapy of HIV infections. At least 30 different classes of NNRTI have been described in the literature and several NNRTIs have been evaluated in clinical trials. Dipyridodiazepinone (nevirapine), benzoxazinone (efavirenz) and bis(heteroaryl) piperazine derivatives (delavirdine) have been approved for clinical use. However, the major drawback to the development and application of NNRTIs is the propensity for rapid emergence of drug resistant strains, both in tissue cell culture and in treated individuals, particularly those subject to monotherapy. As a consequence, there is considerable interest in the identification of NNRTIs less prone to the development of resistance.

Several indole derivatives including indole-3-sulfones, piperazino indoles, pyrazino indoles, and 5H-indolo[3,2-b][1,5]benzothiazepine derivatives have been reported as HIV-1 reverse transciptase inhibitors. Indole 2-carboxamides have also been described as inhibitors of cell adhesion and HIV infection. 3-Substituted indole natural products (Semicochliodinol A and B, didemethylasterriquinone and isocochliodinol) were disclosed as inhibitors of HIV-1 protease.

New drugs for the treatment of HIV are needed for the treatment of patients who become resistant to the currently approved drugs described above which target reverse transcriptase or the protease. One approach to obtaining these drugs is to find molecules which inhibit new and different targets of the virus. A general class of inhibitors which are under active study are HIV entry inhibitors. This general classification includes drugs aimed at several targets which include chemokine receptor (CCR5 or CXCR4) inhibitors, fusion inhibitors targeting viral gp41, and inhibitors which prevent attachment of the viral envelope, gp120, the its human cellular target CD4.

There are two general approaches for preventing the initial attachment of viral membrane, gp120, to cellular CD4 which are a) inhibitors which bind to human CD4 and block attachment of viral envelope (gp120) and b) inhibitors which bind to viral gp 120 and prevent the binding of cellular CD4. The second approach has the advantage that it inhibits a viral target and, if selective, minimizes the chances of perturbing normal human physiology or causing side effects. With this approach, in order to overcome a spectrum in susceptibility to drug caused by variability in the sequences of viral envelope and to suppress the development of resistance, it is important to achieve plasma levels of drug that is as many multiples as possible over the EC50 or other measure of the concentration of drug needed to kill virus. To be of wide utility in human these inhibitors must be able to achieve exposure levels sufficient to enable virus suppression. The higher the multiple of drug levels over the level needed to inhibit viral growth, the more efficiently and completely the suppresion of viral replication and the lower the chance for viral mutation and subsequent development of resistance to treatment. Thus, important aspects contributing to the efficacy of viral attachment inhibitors include not only intrinsic potency and safety, but also pharmacokinetics and pharmaceutical properties which allow attainment of high plasma exposure at a physically feasible dose and an acceptable, preferably convenient, administration schedule.

Indole, azaindole and other oxo amide containing derivatives from this class have been disclosed in a number of different PCT and issued U.S. patent applications. (See (1) Blair et al., Preparation of antiviral indoleoxoacetyl piperazine derivatives U.S. Pat. No. 6,469,006; (2) Wang et al., Antiviral azaindole derivatives. U.S. Pat. No. 6,476,034; (3) Wallace et al., Owen B.; Wang, Tao; Yeung, Kap-Sun; Pearce, Bradley C.; Meanwell, Nicholas A.; Composition and antiviral activity of substituted indoleoxoacetic piperazine derivatives. U.S. patent application Ser. No. 10/027,612 filed Dec. 19, 2001, which is a continuation-in-part application of U.S. Ser. No. 09/888,686 filed Jun. 25, 2001; (4) Wang et al., Composition and antiviral activity of substituted azaindoleoxoacetic piperazine derivatives. U.S. Pat. Appl. Publ. 2003/0207910 A1 published Nov. 6, 2003); (5) Wang et al. Preparation of indole, azaindole, and related heterocyclic piperazinecarboxamides for treatment of AIDS, WO 2002/085301A2; (6) Kadow et al., Preparation of indole, azaindole and related heterocyclic pyrrolidine derivatives as antiviral agents. WO 2003/068221 A1; (7) Wang et al., Bicyclo 4.4.0 antiviral derivatives, WO 2003/092695 A1; (8) Kadow et al., Preparation of indolyl-, azaindolyl-, and related heterocyclic sulfonylureidopiperazines for treatment of HIV and AIDS, WO2004/000210 A2; (9) Wang et al., Composition and antiviral activity of substituted azaindoleoxoacetic piperazine derivatives. U.S. Pat. Appl. Publ. 2004/110785 A1). None of the compounds in these references teaches or suggests an aminium salt of a 1,2,3-triazole.

Prodrug strategies or methodologies can be used to markedly enhance properties of a drug or to overcome an inherent deficiency in the pharmaceutical or pharmacokinetic properties of a drug. Prodrugs are new chemical entity which upon administration to the patient, regenerates the parent molecule within the body. A myriad of prodrug strategies exist which provide choices in modulating the conditions for regeneration of the parent drug, the physical, pharmaceutic, or pharmacokinetic properties of the prodrug, and the functionality to which the prodrug modifications may be attached. However, none of the existing technologies teaches or suggests the specific prodrugs of the present disclosure. The identification of prodrugs with desired properties is often difficult and non straightforward.

SUMMARY OF THE INVENTION

The present disclosure relates to compounds of Formula I, their pharmaceutical formulations; and their use in patients suffering from or susceptible to a virus such as HIV. The compounds of Formula I are effective antiviral agents, particularly as inhibitors of HIV. The compounds of Formula I, which include nontoxic pharmaceutically acceptable salts thereof, have the formula and meaning as described below.

The present disclosure relates to compounds of Formula I

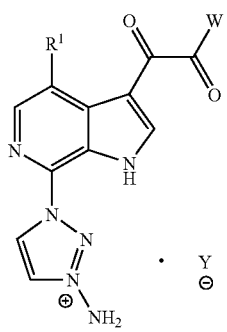

Formula I wherein $R^1$ is selected from the group consisting of hydrogen, halogen and methoxy;

W— is selected from the group consisting of

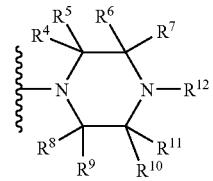

$R^4, R^5, R^6, R^7, R^8, R^9, R^{10}, R^{11}$ are each independently H or methyl; with the proviso that not more than two are methyl;

$R^{12}$ is selected from the group consisting of C(O)-phenyl; and

Y is halogen, O(C)OCH$_3$, OC(O)CF$_3$, or other accept pharmaceutical salt counterion.

A preferred embodiment of Formula I compounds are compounds wherein:

$R^1$ is methoxy or fluoro; and $R^4, R^5, R^6, R^7, R^8, R^9, R^{10}, R^{11}$ are each H.

A more preferred embodiment of Formula I compounds are compounds wherein:

$R^1$ is fluoro; and

Y is Cl.

The present disclosure also relates to a pharmaceutical composition which comprises an antiviral effective amount of a compound of Formula I, including pharmaceutically acceptable salts thereof, and one or more pharmaceutically acceptable carriers, excipients or diluents.

The present disclosure further relates to a pharmaceutical composition of Formula I useful for treating infection by HIV, which additionally comprises an antiviral effective amount of an AIDS treatment agent selected from the group consisting of:

an AIDS antiviral agent;

an anti-infective agent;

an immunomodulator; and

HIV entry inhibitors.

The present disclosure further relates to a method for treating a mammal infected with the HIV virus comprising administering to said mammal an antiviral effective amount of a compound of Formula I, including pharmaceutically accceptable salts thereof, and one or more pharmaceutically acceptable carriers, excipients or diluents.

The present disclosure further relates to a method for treating a mammal infected with the HIV virus comprising administering to said mammal an antiviral effective amount of a compound of Formula I, including pharmaceutically accceptable salts thereof, in combination with an antiviral effective amount of an AIDS treatment agent selected from the group consisting of an AIDS antiviral agent; an anti-infective agent; an immunomodulator; and an HIV entry inhibitor.

The present disclosure also relates to the use of an aminium salt of a 1,2,3-triazole as a prodrug for releasing a parent drug containing the 1,2,3-triazole after removal of the aminium moiety in animals or human.

BRIEF DESCRIPTION OF THE FIGURES

The invention is illustrated by reference to the accompanying drawings described below.

FIG. 1. Pharmacokinetic Study, in vivo data: Oral AUC in Rats Vs. Dose Plots.

DETAILED DESCRIPTION OF THE INVENTION

Since the compounds of the present invention, may possess asymmetric centers and therefore occur as mixtures of diastereomers and enantiomers, the present invention includes the individual diastereoisomeric and enantiomeric forms of the compounds of Formula I in addition to the mixtures thereof.

This disclosure relates to a prodrug approach which greatly enhances the maximum exposure and the ability to increase exposure multiples (i.e., multiples of drug exposure greater than $EC_{50}$ or $EC_{90}$) upon dose escalation of efficacious members of a previously disclosed class of HIV attachment inhibitors.

Specifically, this disclosure relates to an aminium salt of a 1,2,3-triazole. The aminium moiety dramatically increases the utility of the parent compounds by functioning as a prodrug modification that significantly increases the solubility and maximum systemic exposure following dosing of the parent molecules in preclinical animal models used to predict human exposure. The aminium group is removed after dosing to animal species.

This disclosure describes prodrugs of specific indole and azaindole ketopiperazine amides which are extremely effective at improving the oral utility of the parent molecules as antiviral agents particulary as anti HIV drugs. The parent molecules are relatively insoluble, and suffer from dissolution-limited absorption which means as the dose is increased above a maximum level, less and less of the drug dissolves in time to be absorbed into the circulation and they are instead passed through the body to be eliminated as waste. The improvements offered by the prodrug are beneficial, for they allow drug levels in the body to be increased significantly, which provides greater efficacy vs HIV virus and in particular vs less sensitive or more resistant strains. Prodrugs are especially important for this class of drugs since the drugs target the envelope of the HIV virus, a target which varies from strain to strain and thus in which maximum exposure multiples are desired. With the prodrug of the present disclosure, more of the drug will be absorbed and reach the target; and pill burden, cost to the patient and dosing intervals could be reduced. The following discussion and data will show that the prodrugs described in this invention work surprisingly well. They release parent drug extremely quickly and efficiently and enhance the exposure to levels which are higher than reported for many prodrugs.

A successful prodrug strategy requires that a chemically reactive site in a molecule be modified via addition of the prodrug moiety and that later under the desired conditions in the patients the prodrug moiety will unmask and release parent drug. The prodrug molecule must have suitable stability in an acceptable dosage form prior to dosing. In addition, the release mechanism must allow the prodrug to regenerate parent drug efficiently and with kinetics that provide therapeutic levels of parent drug at the disease target.

The triazole nitrogen represents an acceptable point of attachment for a prodrug moiety. The concept of an aminium salt formed by amination of a tertiary nitrogen of a hetero-cycle as a means to enhance oral exposure of a parent drug is to the best of our knowledge, unknown in the art. Without being bound, it is believed that the amino group temporarily alters the physical properties of the drug, and is thus a prodrug which increases the aqueous solubility of the resulting molecule, until it is cleaved in the body by an enzymatic or chemical reaction. As shown in the first equation of the scheme below, an aminium salt of a 1,2,3-triazole containing drug could generate the parent molecule which contains a 1,2,3-triazole as part of it's structure after dosing in vivo to animals or human. As shown in the second equation, the parent HIV inhibitor which contains a 1,2,3-triazole was regenerated from the aminium salt after dosing in rats and similar conversion is predicted for higher species including human.

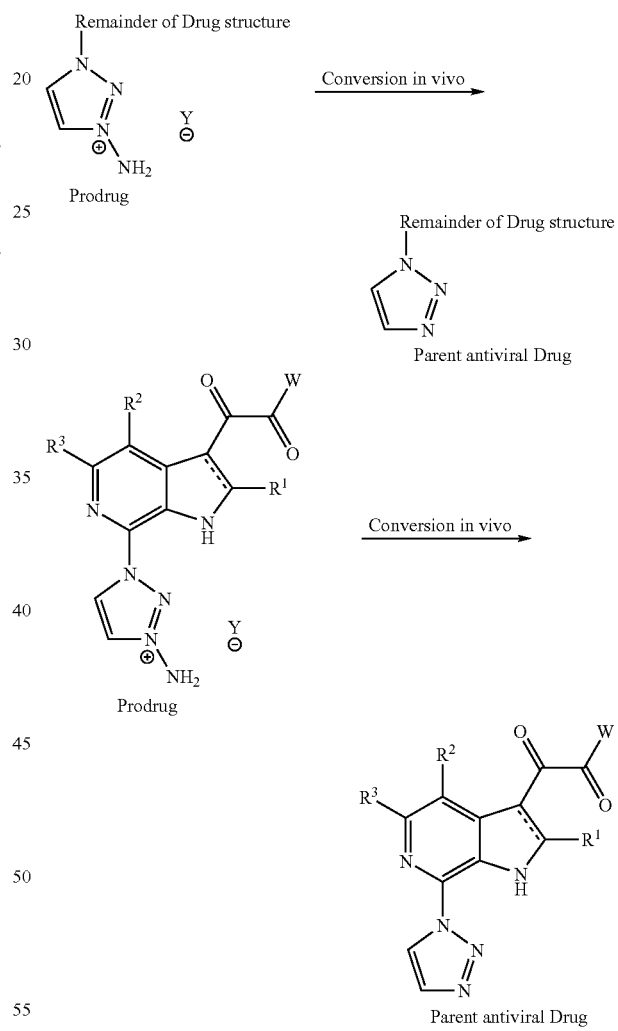

The aminium salts of 1,2,3-triazoles and their pharmaceutically acceptable salts have been shown to have utility as anti HIV agents and enhance the utility of the parent molecules which are being developed as anti-HIV agents which would work by a mechanism, distinct from that of currently approved compounds. These new compounds present a great new opportunities for patients, particularly those who have become resistant to the current drug classes.

We have found that these prodrugs are more water soluble than the parent molecules, and rapidly convert to the parents after oral dosing in rodents. In addition, in one oral dose escalation study, a prodrug provided surprising enhancements in drug exposure (AUC) and maximum concentration (Cmax) as the dose increased.

These studies suggest these prodrugs should provide advantages in animals and humans.

Abbreviations

The following abbreviations, most of which are conventional abbreviations well known to those skilled in the art, are used throughout the description of the invention and the examples. Some of the abbreviations used are as follows:

| | |
|---|---|
| h = | hour(s) |
| rt = | room temperature |
| mol = | mole(s) |
| mmol = | millimole(s) |
| g = | gram(s) |
| mg = | milligram(s) |
| mL = | milliliter(s) |
| TFA = | Trifluoroacetic Acid |
| DCE = | 1,2-Dichloroethane |
| $CH_2Cl_2$ = | Dichloromethane |
| TPAP = | tetrapropylammonium perruthenate |
| THF = | Tetrahydofuran |
| DEPBT = | 3-(Diethoxyphosphoryloxy)-1,2,3-benzotriazin-4(3H)-one |
| DMAP = | 4-dimethylaminopyridine |
| P-EDC = | Polymer supported 1-(3-dimethylaminopropyl)-3-ethylcarbodiimide |
| EDC = | 1-(3-dimethylaminopropyl)-3-ethylcarbodiimide |
| DMF = | N,N-dimethylformamide |
| Hunig's Base = | N,N-Diisopropylethylamine |
| MCPBA = | meta-Chloroperbenzoic Acid |
| azaindole = | 1H-Pyrrolo-pyridine |
| 4-azaindole = | 1H-pyrrolo[3,2-b]pyridine |
| 5-azaindole = | 1H-Pyrrolo[3,2-c]pyridine |
| 6-azaindole = | 1H-pyrrolo[2,3-c]pyridine |
| 7-azaindole = | 1H-Pyrrolo[2,3-b]pyridine |
| 4,6-diazaindole= | 5H-Pyrrolo[3,2-d]pyrimidine |
| 5,6-diazaindole= | 1H-Pyrrolo[2,3-d]pyridazine |
| 5,7-diazaindole= | 7H-Pyrrolo[2,3-d]pyrimidine |
| PMB = | 4-Methoxybenzyl |
| DDQ = | 2,3-Dichloro-5,6-dicyano-1,4-benzoquinone |
| OTf = | Trifluoromethanesulfonoxy |
| NMM = | 4-Methylmorpholine |
| PIP-COPh = | 1-Benzoylpiperazine |
| NaHMDS = | Sodium hexamethyldisilazide |
| EDAC = | 1-(3-Dimethylaminopropyl)-3-ethylcarbodiimide |
| TMS = | Trimethylsilyl |
| DCM = | Dichloromethane |
| DCE = | Dichloroethane |
| MeOH = | Methanol |
| THF = | Tetrahydrofuran |
| EtOAc = | Ethyl Acetate |
| LDA = | Lithium diisopropylamide |
| TMP-Li = | 2,2,6,6-tetramethylpiperidinyl lithium |
| DME = | Dimethoxyethane |
| DIBALH = | Diisobutylaluminum hydride |
| HOBT = | 1-hydroxybenzotriazole |
| CBZ = | Benzyloxycarbonyl |
| PCC = | Pyridinium chlorochromate |

Definitions

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

A "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyltriazine, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

A "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encomplish systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, amino, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1–20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(=O)O-group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$— groups with Z as defined above.

A "trihalomethanesulfonamido" group refers to a $Z_3CS$(=O)$_2NR^x$— group with Z and $R^x$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—.

A "S-sulfonamido" group refers to a —S(=O)$_2NR^xR^Y$, with $R^X$ and $R^Y$ as defined herein.

A "N-Sulfonamido" group refers to a R"S(=O)$_2NR_X$— group with $R_x$ as defined herein.

A "O-carbamyl" group refers to a —OC(=O)$NR^xR^y$ as defined herein.

A "N-carbamyl" group refers to a $R^xOC$(=O)$NR^y$ group, with $R^x$ and $R^y$ as defined herein.

A "O-thiocarbamyl" group refers to a —OC(=S)$NR^xR^y$ group with $R^x$ and $R^y$ as defined herein.

A "N-thiocarbamyl" group refers to a $R^xOC$(=S)$NR^y$— group with $R^x$ and $R^y$ as defined herein.

An "amino" group refers to an —$NH_2$ group.

A "C-amido" group refers to a —C(=O)$NR^xR^y$ group with $R^x$ and $R^y$ as defined herein.

A "C-thioamido" group refers to a —C(=S)$NR^xR^y$ group, with $R^x$ and $R^y$ as defined herein.

A "N-amido" group refers to a $R^xC$(=O)$NR^y$— group, with $R^x$ and $R^y$ as defined herein.

An "ureido" group refers to a —$NR^xC$(=O)$NR^yR^{y2}$ group with $R^x$ and $R^y$ as defined herein and $R^{y2}$ defined the same as $R^x$ and $R^y$.

An "thioureido" group refers to a —$NR^xC$(=S)$NR^yR^{y2}$ group with $R^x$ and $R^y$ as defined herein and $R^{y2}$ defined the same as $R^x$ and $R^y$.

A "guanidino" group refers to a —$R^xNC$(=N)$NR^yR^{y2}$ group, with $R^x$, $R^y$ and $R^{y2}$ as defined herein.

A "guanyl" group refers to a $R^xR^yNC$(=N)— group, with $R^x$ and $R^Y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with $R^x$ as defined herein.

A "hydrazino" group refers to a —$NR^xNR^yR^{y2}$ group with $R^x$, $R^y$ and $R^{y2}$ as defined herein.

Any two adjacent R groups may combine to form an additional aryl, cycloalkyl, heteroaryl or heterocyclic ring fused to the ring initially bearing those R groups.

It is known in the art that nitogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts of the prodrug compounds disclosed herein are within the scope of this invention. The term "pharmaceutically acceptable salt" as used herein and in the claims is intended to include nontoxic base addition salts. The term "pharmaceutically acceptable salt" as used herein is also intended to include salts of acidic groups, such as a carboxylate or phosphate or phosphate mono ester, with such counterions as ammonium, alkali metal salts, particularly sodium or potassium, alkaline earth metal salts, particularly calcium or magnesium, transition metal salts such as zinc and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), lysine, arginine, histidine, N-methylglucamine, or with bases such as piperidine or morpholine. In the case of phosphate monoesters, the possibility of mono or bis exists and both are covered by this invention. Stoichiometry possibilities are well known to those in the art. Discussions of pharmaceutically acceptable salts and lists of possible salts are contained in the following references:

*Preparation of water-soluble compounds through salt formation*. Stahl, P. Heinrich. Cosmas Consult, Freiburg im Breisgau, Germany. Editor(s): Wermuth, Camille Georges. Practice of Medicinal Chemistry (2nd Edition) (2003), 601–615. Publisher: Elsevier, London, UK CODEN: 69EOEZ

*Handbook of pharmaceutical salts: properties, selection, and use*/by Stahl, P. Heinrich., Wermuth, Camille G., International Union of Pure and Applied Chemistry. Weinheim; New York: VHCA; Wiley-VCH, 2002.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following tables.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)6-Chloro-4-(S)-cyclopropylethynyl-4(S)-trifluoro-methyl-1,4-dihydro- | DuPont Merck | HIV infection, AIDS, ARC (non-nucleoside RT inhibitor) |

-continued

| Drug Name | Manufacturer | Indication |
|---|---|---|
| 2H-3,1-benzoxazin-2-one, STOCRINE | | |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-thymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (or T-20) | Roche/Trimeris | HIV infection AIDs, viral Fusion inhibitor |
| Lexiva ® (or Fosamprenavir calcium) | GSK/Vertex | HIV infection AIDs, viral protease inhibitor |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |

| Drug Name | Manufacturer | Indication |
|---|---|---|
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with other HIV entry inhibitors. Non-limiting examples of such HIV entry inhibitors are discussed in DRUGS OF THE FUTURE 1999, 24(12), pp. 1355–1362; CELL, Vol. 9, pp. 243–246, Oct. 29, 1999; and DRUG DISCOVERY TODAY, Vol. 5, No. 5, May 2000, pp. 183–194 and Inhibitors of the entry of HIV into host cells. Meanwell, Nicholas A.; Kadow, John F. Current Opinion in Drug Discovery & Development (2003), 6(4), 451–461. Specifically the compounds can be utilized in combination with other attachment inhibitors, fusion inhibitors, and chemokine receptor antagonists aimed at either the CCR5 or CXCR4 coreceptor.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments of with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is Reyataz® (active ingredient Atazanavir). Typically a dose of 300 to 600 mg is administered once a day. This may be co-administered with a low dose of Ritonavir (50 to 500 mgs). Another preferred inhibitor of HIV protease is Kaletra®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

Detailed Chemistry

1. Preparation of Produg Molecules:

The present invention comprises compounds of Formula I, their pharmaceutical formulations, and their use in patients suffering from or susceptible to HIV infection.

Scheme A depicts an overview of the currently preferred strategy for preparing the prodrugs of the invention from the parent molecules (Formula IV).

Scheme A

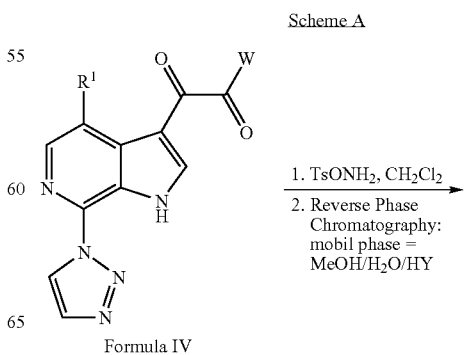

1. TsONH$_2$, CH$_2$Cl$_2$
2. Reverse Phase Chromatography: mobil phase = MeOH/H$_2$O/HY Formula IV

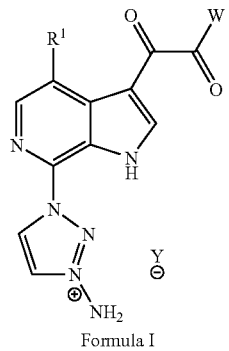

Formula I

To elaborate on the method, as shown in Scheme A, the antiviral parent compound of interest, IV, is converted into the aminium salt of formula I, by N-amination with an excess (1.1 to 100 equivalents) of with O-p-tolylsulphonyl-hydroxylamine (TsONH$_2$) in a solvent such as methylene chloride. Alternative other aminating agents can be used i.e. O-(2,4-dinitrophenyl)hydroxylamine (DnpONH$_2$), O-(diphenylphosphinyl)-hydroxylamine (DppONH$_2$), O-(mesitylenesulfonyl)hydroxylamine (MtsONH$_2$) and O-mesitoylhydroxylamine (MtONH$_2$) (Nomenclature taken from Shen Y. et al. J. Org. Chem. 2002, 67, 6236). The mixture is usually stirred at rt for a period of 1 to 48 h. After removing the solvent in vacuo, the residue is redisolved in methanol or acetonitrile or a mixture of either one with water and purified by reverse chromatography using a mixture of water with methanol or acetonitrile and a 1% of an acid (YH) such as HCl or CF$_3$COOH. Additionally the counterion can be exchange by passing the resulting salt through and ion exchange column.

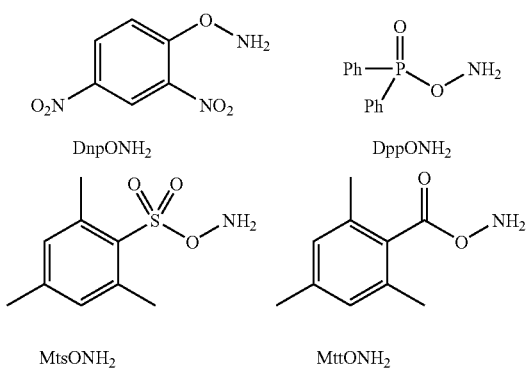

All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

| LC/MS Method (i.e., compound identification) | |
|---|---|
| Column A: | YMC ODS-A S7 3.0 × 50 mm column |
| Column B: | PHX-LUNA C18 4.6 × 30 mm column |
| Column C: | XTERRA ms C18 4.6 × 30 mm column |
| Column D: | YMC ODS-A C18 4.6 × 30 mm column |

| LC/MS Method (i.e., compound identification) | |
|---|---|
| Column E: | YMC ODS-A C18 4.6 × 33 mm column |
| Column F: | YMC C18 S5 4.6 × 50 mm column |
| Column G: | XTERRA C18 S7 3.0 × 50 mm column |
| Column H: | YMC C18 S5 4.6 × 33 mm column |
| Column I: | YMC ODS-A C18 S7 3.0 × 50 mm column |
| Column J: | XTERRA C-18 S5 4.6 × 50 mm column |
| Column K: | YMC ODS-A C18 4.6 × 33 mm column |
| Column L: | Xterra MS C18 5 uM 4.6 × 30 mm column |
| Column M: | YMC ODS-A C18 S3 4.6 × 33 mm column |

Standard LC Run Conditions (Used Unless Otherwise Noted):

| | |
|---|---|
| Gradient: | 100% Solvent A/0% Solvent B to 0% Solvent A/ 100% Solvent B<br>Solvent A = 10% MeOH—90% H$_2$O - 0.1% TFA, Solvent B = 90% MeOH—10% H$_2$O - 0.1% TFA; and R$_t$ in min. |
| Gradient time: | 2 minutes |
| Hold time | 1 minute |
| Flow rate: | 5 mL/min |
| Detector Wavelength: | 220 nm |
| Solvent A: | 10% MeOH/90% H$_2$O/0.1% Trifluoroacetic Acid |
| Solvent B: | 10% H$_2$O/90% MeOH/0.1% Trifluoroacetic Acid |

Alternate LC Run Conditions B:

| | |
|---|---|
| Gradient: | 100% Solvent A/0% Solvent B to 0% Solvent A/ 100% Solvent B<br>Solvent A = 10% MeOH—90% H$_2$O - 0.1% TFA, Solvent B = 90% MeOH—10% H$_2$O - 0.1% TFA; and R$_t$ in min. |
| Gradient time: | 4 minutes |
| Hold time | 1 minute |
| Flow rate: | 4 mL/min |
| Detector Wavelength: | 220 nm |
| Solvent A: | 10% MeOH/90% H$_2$O/0.1% Trifluoroacetic Acid |
| Solvent B: | 10% H$_2$O/90% MeOH/0.1% Trifluoroacetic Acid |

Compounds purified by preparative HPLC were diluted in MeOH (1.2 mL) and purified using the following methods on a Shimadzu LC-10A automated preparative HPLC system or on a Shimadzu LC-8A automated preparative HPLC system with detector (SPD-10AV UV-VIS) wavelength and solvent systems (A and B) the same as above.

| Preparative HPLC Method (i.e., compound purification) | |
|---|---|
| Purification Method: | Initial gradient (40% B, 60% A) ramp to final gradient (100% B, 0% A) over 20 minutes, hold for 3 minutes (100% B, 0% A) |
| Solvent A: | 10% MeOH/90% H$_2$O/0.1% Trifluoroacetic Acid |
| Solvent B: | 10% H$_2$O/90% MeOH/0.1% Trifluoroacetic Acid |
| Column: | YMC C18 S5 20 × 100 mm column |
| Detector Wavelength: | 220 nm |

For the experimental procedures below the following HPLC conditions or modifications from the standard procedures were employed:

HPLC Conditions for Routine LC Purity:
Detection at 254 nm; Gradient 0–100% B/A; A 10% CH3CN-90% H2O-0.1% TFA, B 90% CH3CN-10% H2O-0.1% TFA; Gradient time 4 min; Column YMC ODS-AQ or ORD-A 4.6×50 mm 3 micron.

HPLC Conditions for LC/MS Analysis:
Column J: XTERRA C-18 S5 4.6×50 mm column, Gradient: 100% Solvent A/0% Solvent B to 0% Solvent A/100% Solvent B
Solvent A=10% MeOH-90% H2O-0.1% TFA, Solvent B=90% MeOH-10% H2O-0.1% TFA; and Rt in min; Gradient time: 3 minutes; Flow rate: 4 mL/min; Detector Wavelength: 220 nm Starting materials, can be purchased from commercial sources or prepared using literature procedures.

2. Preparation of Parent Molecules:

The preparation of parent molecules (Formula IV) were disclosed previously, generally and/or specifically, in
U.S. Pat. No. 6,499,006 granted Oct. 22, 2002 to W. S. Blair et al;
U.S. Pat. No. 6,476,034 granted Nov. 5, 2002 to Wang et al;
U.S. Pat. No. 6,573,262 granted Jun. 3, 2003 to Meanwell et al;
U.S. Ser. No. 10/630,278 filed Jul. 30, 2003 to J. Kadow et al; which is a continuation-in-part of U.S. Ser. No. 10/214,982 filed Aug. 7, 2002, which is a continuation-in-part of U.S. Ser. No. 10/038,306 filed Jan. 2, 2002, which corresponds to PCT WO 02/062423, filed Jan. 2, 2002, published Aug. 15, 2002;
U.S. Provisional Ser. No. 60/541,970 filed Feb. 5, 2004 to Yeung et al; and
U.S. Ser. No. 10/762,108 filed Jan. 21, 2004 to Wang et al, corresponding to PCT/US03/13324 filed Apr. 30, 2003.

Select detailed procedures are illustrated below in Example 1.

Biology and Compound Administration/Formulation

The prodrugs of the present disclosure have demonstrated efficacy in animal studies.

The compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections such as HIV infection and AIDS. The treatment involves administering to a patient in need of such treatment a pharmaceutical composition comprising a pharmaceutical carrier and a therapeutically-effective amount of a compound of the present invention.

The pharmaceutical composition may be in the form of orally-administrable suspensions or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds of this invention can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is further described in the following non-limiting examples.

EXAMPLES

Example 1

Synthesis of Compound I-a

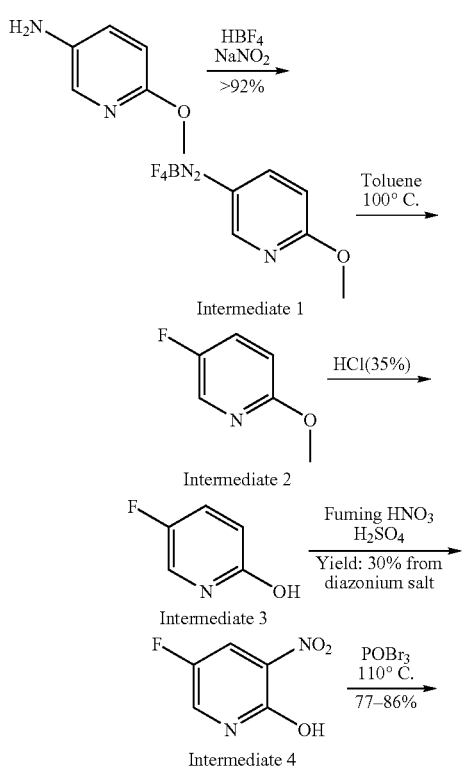

Intermediate 1

Intermediate 2

Intermediate 3

Intermediate 4

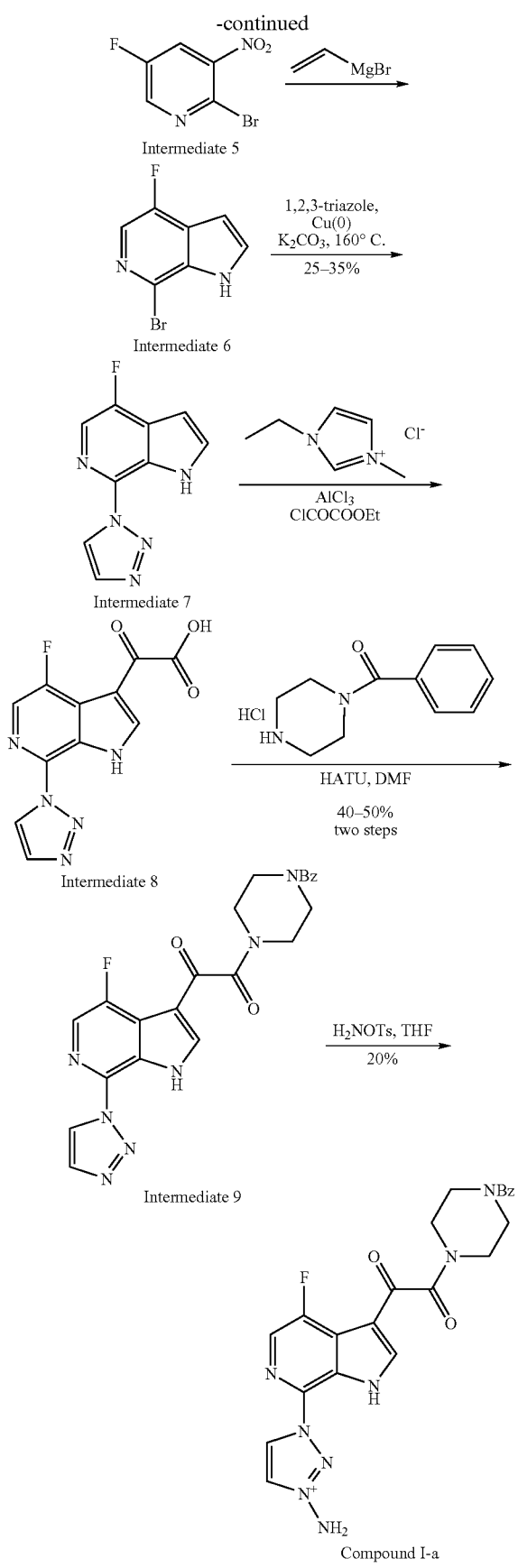

Experimental Procedures:

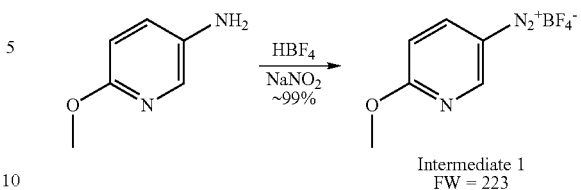

5-Amino 2 methoxypyridine (50 g, 0.4 mol) was added to a stirring mixture of absolute ethanol (280 ml) and HBF$_4$ (48% in water, 172 ml) and cooled to 0° C. Sodium nitrite (129 g) was dissolved in water (52 ml) and added portionwise over 1 h). The stirring was continued at 0° C. for 2 hr. The reaction mixture was diluted with ether (1 L). The solid product was collected by filtration and washed with 500 ml of 50:50 EtOH/ether and subsequently several times with ether until the product was slightly pinkish in color. The pale pink solid 90 g, intermediate 1 (~100% yield) was kept in a dessicator over P$_2$O$_5$.

The same procedure was followed to perform the reaction on larger scale:

(1) (200 g, 1.6 mol); HBF$_4$ (688 ml); NaNO$_2$ (116 g); EtOH (1.12 L); H$_2$O (208 ml)

The reaction was run 4 times (total 800 grams (1–80)). The product was dried over P$_2$O$_5$ for 48 hr. (only 24 hr for first batch).

A total of 1,293 Kg of intermediate 1 was obtained, (91% yield).

Ref: *J. Heterocyclic Chem.*, 10, 779, 1973 (for above reactions, including analytical data)

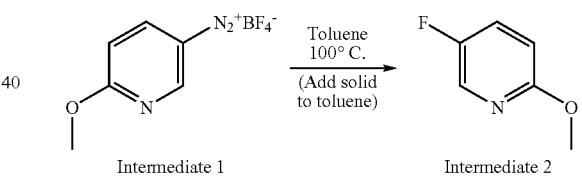

The decomposition of the diazonium salt (intermediate 1) was run in 3 batches of: 206 g, 219 g and 231 g using 1.3 L, 1.4 L and 1.6 L of anhydrous toluene respectively. The toluene was preheated under nitrogen to 100° C. (internal temperature) in a 2 L 3-neck round bottom flask provided with a mechanical stirrer. The solid was added solid portionwise via a scoop through a powder funnel which was attached to an adapter with slight outward positive nitrogen flow. During addition, the temperature was maintained between 99–102° C. (set at 100° C.) and stirred vigorously. Total addition time was 60 min. for the smaller two batches and 70 min. for the last one. After the addition was finished, each stirring reaction was heated at 110° C. for 1 hr. The heating mantle was removed and stirring was stopped. The reactions were allowed to stand for 2 hr (ambient temp achieved). The reaction contained BF$_3$ so extra caution was taken. The hot toluene from the reaction was poured into a 4 L Erlenmeyer (a dark brown oil and residue remained in the flask). The residue was washed with 50 ml of toluene and poured into the original toluene extracts.

Add 1.5 L of 1N NaOH to toluene layer, extract and wash with ~100 ml of sat aq. NaCl.

Combine NaCl with NaOH layer, re-extract with 150 ml of toluene, wash with 50 ml of sat NaCl.

Combine toluene layers.

Add 1 L of 1N NaOH to residue in reaction flask and swirl to dissolve as much residue as possible then add 500 ml Et$_2$O and pour into Erlenmeyer.

Add ~500 ml more of 1 N NaOH to reaction flask and swirl ~500 ml of Et$_2$O.

Combine dark Et$_2$O and NaOH washings in erlenmyer flask.

Et$_2$O/NaOH mixture was poured through powder funnel containing plug of glass wool to collect dark viswcous solid. (Add ~500 ml more ether to wash) into 6 L sep funnel.

Extract. Wash ether layer with ~200 ml of H$_2$O and then 100 ml of sat NaCl.

Combine all washings with original NaOH aq. Layer and re-extract with 500 ml of ether. Wash with 100 ml H$_2$O and 100 ml of NaCl.

Combine ether extracts. Toluene and ether extracts were checked by LC/MS clean product (intermediate 2).

The ether was concentrated on a rotovap and the residue was combined with the toluene extracts to make a homogeneous solution which is taken to next step as is.

The other two rxns were combined and worked up in the same way.

All aqueous layers were checked by LC/MS=no product.

Ref: *J. Heterocyclic Chem.*, 10, 779, 1973 (for above reactions, including analytical data)

Intermediate 2 → Intermediate 3

A total of 4.6 L of toluene solution containing intermediate 2 was placed in several sealed tubes and treated with 900 ml of 35% HCl at 145° C. for 2 hr. LC/MS showed no starting material, only 4. The toluene solution was decanted and discarded. The aqueous phase was washed with EtOAc and concentrated down to remove volatiles to afford a brown solid containing the desired fluoro-hydroxypyridine (intermediate 3).

A total of 244 g of this solid was collected and taken to next step as is (it was not completely dry).

Note: We have subsequently run this by decanting the toluene layer first prior to heating to reduce volumes. Same reaction was carried out using HBr (48% in H2O) at 100° C. for 6 h with similar result to the literature procedure 49% yield.

Ref: *J. Heterocyclic Chem.*, 10, 779, 1973 (for above reactions, including analytical data)

Intermediate 3 → Intermediate 4

1. Precipitate (usually)
2. Extracted with EtOAc, triturated with ether

The solid from above containing intermediate 3 was divided in 4 batches and treated with H$_2$SO$_4$ and fuming HNO$_3$ as shown below. The amounts used were:

|   | batch 1 | batch 2 | batch 3 | batch 4 |
|---|---|---|---|---|
| (1) | 25 g | 54 g | 75 g | 90 g |
| fuming HNO$_3$ | 20.8 ml | 45 ml | 62.4 ml | 75 ml |
| H$_2$SO$_4$ (for addition) | 5.6 ml+ | 12 ml+ | 16.8 ml+ | 20 ml+ |
| (for soln) | 56 ml | 120 ml | 168 ml | 200 ml |

Intermediate 3 was dissolved in sulfuric acid (the larger amounts indicated above) at rt and then heated to 65° C. A preformed solution of fuming nitric acid and sulfuric acid (the smaller amount indicated above) was added dropwise. The temperature was kept between 65° C. and 80° C. (rxn is exothermic and although the bath is at 65° C., temperature goes higher, usually 75, sometimes 80° C.). After the addition was complete, the reaction mixture was heated at 65° C. for an additional hr. The reaction mixture was then cooled to rt and poured in a flask containing ice) (20 g of ice/gr compound, evolution of gas occurred). A solid precipitated out and it was collected by filtration ($^1$HNM" showed intermediate 4 and something else (discarded)).

The aqueous layer was extracted with AcOEt several times (3–5) and concentrated on a rotary evaporator under vacuum to afford a solid that was triturated with ether to afford intermediate 4 as a bright yellow solid. A total of 117 g of desired product was collected in the first crop (27% yield from diazonium salt). A portion did not crystallize: this oil was triturated with MeOH and Et$_2$O to afford 3.6 g of intermediate 4; another precipitation from the mother liquid afforded an additional 6.23 g of the desired product intermediate 4.

Total: 117.0+3.6+6.23=126.83. 30.4%). Yield for 3 steps (decomposition of diazonium salt; deprotection and nitration).

Analytical data from Notebook: 53877–115: $^1$HNMR($\delta$, MeOD): 8.56–8.27 (dd, J=7.5, 3.3 Hz, 1H), 8.01 (d, J=3.3 Hz, 1H); LC/MS(M+1)$^+$=158.9; rt=0.15 min.

Note: A portion of the aqueous acidic solution was taken and neutralized with Na$_2$CO$_3$ until effervescence stopped and then it was extracted with AcOEt⇒ A different product was obtained. No desired product in these extracts.

Intermediate 4 → Intermediate 5 (Used without purification)

A total of 117 g of intermediate 4 was divided in 4 batches of 30 g×3 and 27 g×1 and treated with POBr$_3$ (3 equiv.; 163 g×3 and 155 g×1) and a catalytic amount of DMF (15 ml) at rt (DMF was added carefully⇒gas evolution). After 5 min. at room temperature, the solutions were heated at 110° C. for 3 hr. LC/MS showed starting material had been consumed. The reaction mixtures were allowed to cool to rt.

The reaction flasks were placed in an ice bath; and then ice was added very slowly and carefully portionwise into the flask, gas evolution was due to HBr formation; the liquid and black solid that formed was poured into a beaker with ice. EtOAc was added and the mixture was then extracted several times with EtOAc. The organic layer was washed with saturated aq. NaHCO₃; H₂O and brine; dried over Na₂SO₄ and filtered. The product was dried in the pump overnight to provide 123 g of intermediate 5 as a brown solid (77% yield).

Note: Reaction is completed within 1 h.

¹HNMR(δ, CDCl₃): 8.52 (m, 1H), 7.93 (m, 1H).

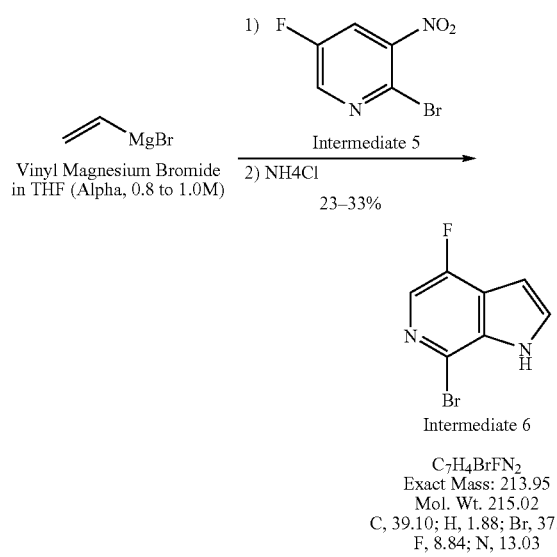

800 ml of vinyl magnesium bromide (1M in THF, Aldrich) was cooled below −60° C. with vigorous stirring under N₂. 2-bromo-5-fluoro-3-nitro pyridine (43.3 g, 0.196 mol) in 200 ml THF was added dropwise via addition funnel at such a rate that the temp was kept below −60° C. This took ~1.25 hr. The reaction mixture was warmed to −40 to −50° C. and stirred for 1 hr more. Then 1 L of saturated aqueous NH₄Cl was added slowly and cautiously. At first, foaming occurred and considerable solid was present, but this essentially dissolved as the addition was completed and the material warmed to rt. The layers were separated and the aqueous layer extracted 3 times with ethyl acetate. The organic extracts were washed with brine, dried over Na₂SO₄, filtered and concentrated to afford ~50 g of a black gummy solid. HPLC indicated 57–58% product. To this was added CH₂Cl₂ and the solid was collected by filtration and washed with CH₂Cl₂ to afford 12.5 g of product as a brown solid. The reaction was repeated on exactly the same scale and worked up in the same manner. From CH₂Cl₂ trituration there was obtained 12.4 g of Intermediate 6 (HPLC ~97% pure). The crude was recovered and allowed to stand in dichloromethane. Upon standing 3.6 g of additional product separated and was recovered by filtration.

Total yield=29.5 g (35%).

¹HNMR(δ, CDCl₃): 8.69 (bs, 1H), 7.92 (d, J=1.8 Hz, 1H), 7.41 (m, 1H), 6.77 (m, 1H); LC/MS(M+1)⁺=216.–217.9; rt 1.43 min.

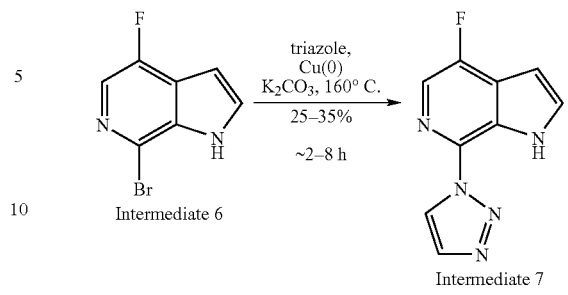

Reaction was carried in a 250 ml flask (foaming occurred upon heating and the big size flask is more convenient). A mixture of intermediate 6 (3 g, 13.95 mmol), 1,2,3-triazole (15 g, 217.6 mmol, 15 eq), K₂CO₃ (1.9 g, 13.95 mmol, 1 eq) and Cu(0) (0.9 g, 13.9 mmol, 1 eq) was heated at 160° C. for 7 hr (from rt to 160° C. total 7 hr) under N₂ (depending on the Cu(0) lot, reaction time may vary from 2 hr to 7 hr). The resulting mixture was diluted with MeOH, filtered through filter paper (to remove the copper). Washed with MeOH (20 ml) and water (30 ml).

The filtrate was concentrated (remove solvent in rotovap) and diluted with ethylacetate. The aqueous layer was extracted with ethylacetate. The combined organic layer was dried over sodium sulfate, filtered and concentrated. The residue was dissolved in MeOH (20 ml), intermediate 7 (750 mg) crystallized from the methanol as a white solid and was collected by filtration. (Slow gradient volume, silica gel hex/AcOEt (0→18%) of the mother liquids usually affords 5–10% more of intermediate 7.

¹HNMR (δ, CDCl₃): 10.47 (bs, 1H), 8.76 (s, 1H), 7.94 (s, 1H), 7.89 (s, 1H), 7.53 (m, 1H), 6.78 (m, 1H); LCMS(M+1)⁺=204; rt=1.29 min.

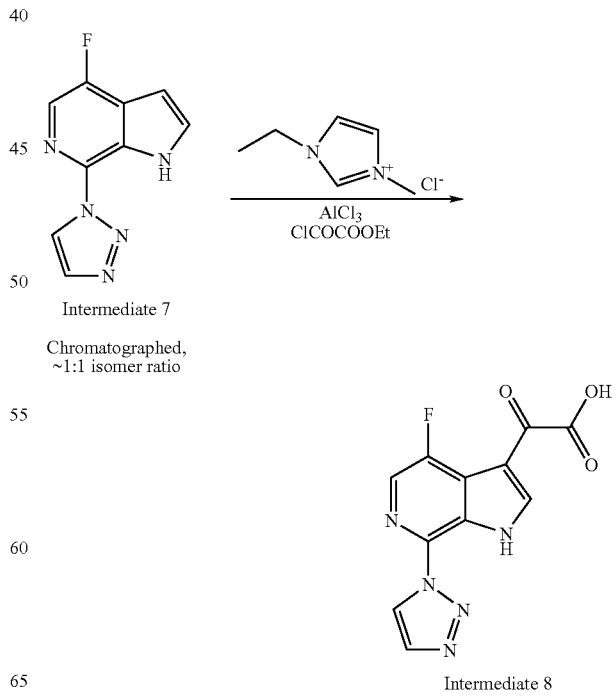

Ethyl methylimidazolium chloride (4.3 g, 29.6 mmol, 3 eq) was placed in a 250 ml flask. AlCl$_3$ (11.8 g, 88.6 mmol, 9 eq) was added into the flask in one portion. A liquid suspension was formed (some of AlCl$_3$ remained as solid). After stirring for 5–10 min. intermediate 7 (2.0 g, 9.85 mmol) was added in one portion followed by slow addition (via a syringe) of ethyl chlorooxalacetate (3.3 ml, 29.6 mmol, 3 eq). The reaction was stirred at room temperature for 20 hr. LCMS indicated a mixture of intermediate 8: intermediate 7=6:2. (intermediate 7 has strong UV absorption) The reaction was quenched by carefully adding ice water (~75 ml) at 0° C. A yellow solid precipitated at this point. The resulting suspension was filtered and the solid was washed with water. MeOH and ethyl acetate (to remove unreacted SM) and the solid was dried in air. (LCMS purity 70%~80%) 2 g of solid containing intermediate 8 was obtained and taken to the next step without further purification. LCMS(M+1)$^+$=276; rt=0.97 min.

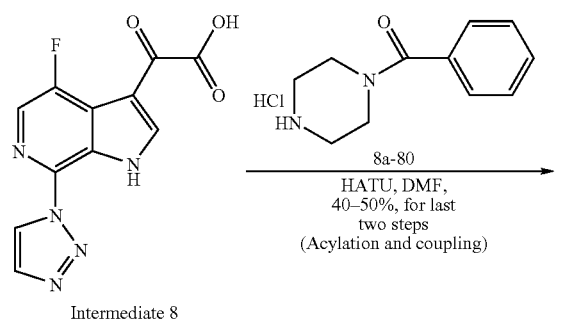

Intermediate 8

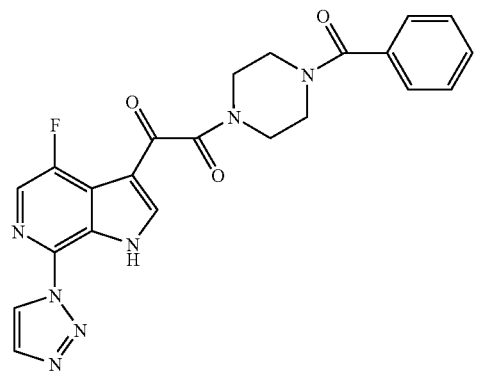

Intermediate 9

A mixture of compound intermediate 8 (4.9 g, 17.8 mmol) and N-benzoylpiperazine hydrochloride (HCl salt; 6.0 g, 26.7 mmol, 1.5 eq) in DMF (30 ml) was stirred at rt overnight (16 hr). A slurry was formed. An additional 20 ml of DMF was added into the slurry. Then HATU (12.2 g, 26.7 mmol, 1.5 eq) was added followed by DMAP (4.3 g, 35.6 mmol, 2 eq). The reaction mixture was stirred for 30 min. LCMS indicated the starting material intermediate 8 was completely converted to product (intermediate 9). The resulting mixture was filtered and the solid washed with water. The filtrate was concentrated in vacuo. Water was added to the residue and the solid was collected by filtration. The solids were combined and washed with water, MeOH and EtOAc. Then the solid was dried in air. LCMS & HPLC showed BMS-248, >99% pure. The solid product was further purified by precipitation and crystallization in 5~10% CH$_3$OH/CHCl$_3$.

$^1$HNMR (d, DMSO) 13.1 (bs, 1H), 9.0 (s, 1H), 8.4 (s, 1H), 8.3 (s, 1H), 8.2 (s, 1H), 7.4 (bs, 5H), 3.7 (bs, 4H), 3.5 (bs, 4H); MS m/z 448 (MH). Anal: Calc for C$_{22}$H$_{18}$FN$_7$O$_3$; C, 59.05; H, 4.05; N, 21.91; F, 4.24. Found; C, 57.28; H, 4.14; N, 21.22; F, 4.07%.

1-Amino-3-{3-[2-(4-benzoyl-piperazin-1-yl)-2-oxo-acetyl]-4-fluoro-1H-pyrrolo[2,3-c]pyridin-7-yl}-3H-[1,2,3]triazol-1-ium trifluoroacetate,

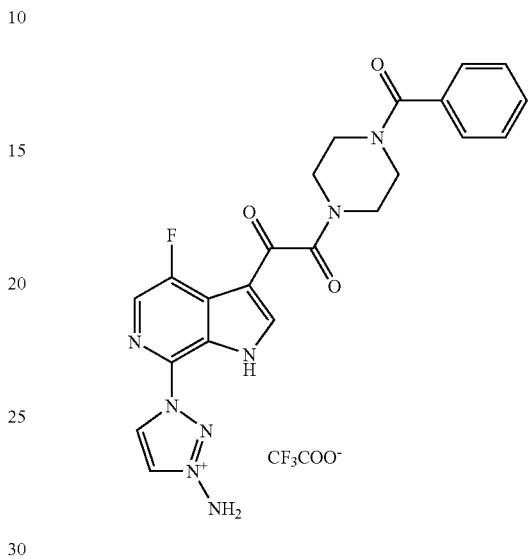

was prepared as follows:

1-(4-Benzoyl-piperazin-1-yl)-2-(4-fluoro-7-[1,2,3]triazol-1-yl-1H-pyrrolo[2,3-c]pyridin-3-yl)-ethane-1,2-dione (intermediate 9) (160 mg, 0.35 mmol) was treated with 5 mL of a CH$_2$Cl$_2$ solution of H$_2$NOTs (prepared as indicated below) and stirred at room temperature for 3 h. The solvent was removed in vacuo and the residue was dissolved in MeOH and purified using reverse phase HPLC to afford the title compound, example 1 as a pale yellow solid (TFA$^-$ salt, 40 mg, 20%). LC/MS: (ES$^+$) m/z (M)$^+$=463. Rt=0.90 min. (HPLC method: XTERRA 3.0×50 mm S7, 0 to 100% B over 2 min, 5 mL/min, A: 10% MeOH/water+0.1% TFA; B: 90% MeOH/water+0.1% TFA). $^1$HNMR (500 MHz, MeOD) 9.49 (s, 1H), 8.81 (s, 1H), 8.51 (s, 1H), 8.26 (s, 1H), 7.48 (bs, 5H), 4.10–4.60 (m, 8H).

The above described TFA$^-$ salt can be used to make the Cl$^-$ salt (1-Amino-3-{3-[2-(4-benzoyl-piperazin-1-yl)-2-oxo-acetyl]-4-fluoro-1H-pyrrolo[2,3-c]pyridin-7-yl}-3H-[1,2,3]triazol-1-ium chloride):

The TFA$^-$ salt (145.0 mg), was taken up in 100 ml water, and applied as a milky suspension to a small open end column packed with 12.1 g BioRad AG 1×2 (analytical grade resin, 100–200 mesh, Cl$^-$ form) anion exchange resin. The resin was pre-equilibrated with 200 ml water. The column was washed with an additional 100 ml water/20 ml methanol. And the combined eluents were lyophilized to afford the title compound as a pale yellow solid (92.4 mg. yield 74%). MS m/z: 463.13. Rt: 1.45 min. (HPLC method: Waters Atlantis 4.6×50 mm S5, 0 to 100% B over 2 min, 5 mL/min, A: 10% MeOH/water+0.1% TFA; B: 90% MeOH/water+0.1% TFA). $^{19}$FNMR(CDCl$_3$): No F detected. $^1$HNMR(500 MHz, CDCl$_3$) 8.96–7.89 (m, 4H), 7.44 (bs, 5H), 4.37–3.46 (m, 8H).

Preparation of H₂NOTs

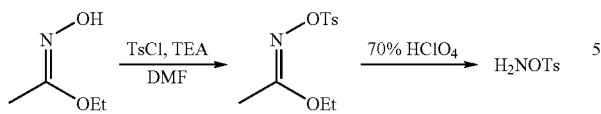

Experimental procedure: J. Chem. Soc. Chem. Com. 1980, 560.

Tosyl chloride (2.1 g, 11.0 mmol) was added in portions to a solution of ethyl N-hydroxyacetimidate (1.2 g, 11.6 mmol) and triethylamine (8.88 mL, 63.7 mmol) in anhydrous DMF (20 mL) at 0° C. After addition is completed, the mixture was placed at room temperature and stirred for 1 h. The reaction mixture was poured over ice-water (100 mL) and stirred for 10 min. A white-yellowish solid was formed and collected by filtration. The solid was washed with water (3×50 mL). (1.3 g of the solid was collected LC/MS: (ES⁺) m/z (M+1)⁺=258. Rt=1.52 min.

This solid was treated with 70% HClO₄ (5 mL) and stirred at rt for 10 min, then in a water bath at 60° C. for 1 min and again at room temperature for 20 min. H₂O (100 mL) was added and the reaction was extracted with CH₂Cl₂ (50 mL). The organic layer was washed with H₂O (50 mL), dried over sodium sulfate, filtered and used as is.

Example 2

Intravenous Injection and Oral Rat PK Study Protocol of the Aminium Prodrug

The TFA⁻ salt made in Example 1 (prodrug I-a) was administered to groups of three male Sprague-Dawley rats by Intravenous bolus (1 mg/kg; all doses were equivalent of its parent compound IV-a) or oral gavage (5 mg/kg). The three rats used in oral dosing study were fasted overnight. The dosing solution was prepared in PEG-400/ethanol (90/10, v/v) at 1 mg/mL (dosing solution concentration was Parent compound IV-a equivalent) for both intravenous and oral administration.

Prodrug I-a:

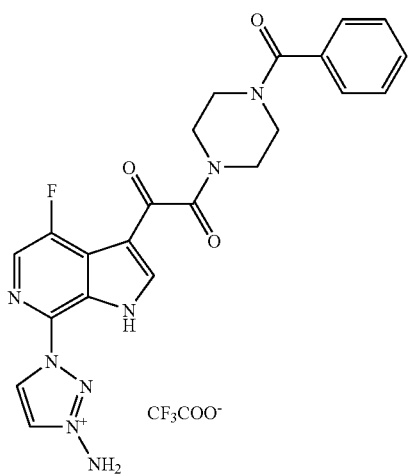

Parent Compound IV-a:

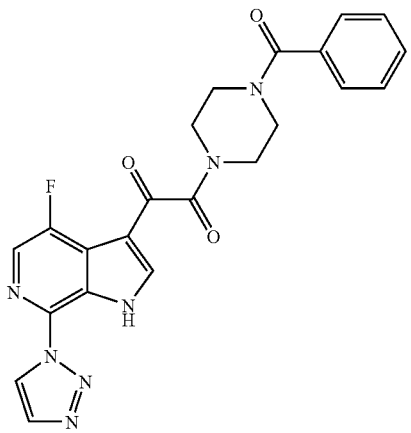

In the oral dose escalation study in rats, Prodrug I-a was administered to groups of three male Sprague-Dawley rats by oral gavage at 5, 25, and 200 mg/kg (Parent compound IV-a equivalent). The dosing solutions were prepared in water with 0.5% methylcellulose.

Plasma samples from the above studies were collected in EDTA vacutainers over 24 hrs, and analyzed by LC/MS/MS for both Prodrug I-a and Parent compound IV-a. Pharmacokinetic analysis was performed using Kinetica™ (See FIG. 1).

What is claimed is:

1. A compound of Formula I, or pharmaceutically acceptable salts thereof,

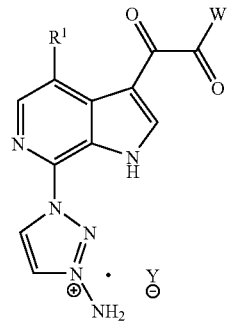

Formula I wherein:
R¹ is selected from the group consisting of hydrogen, halogen and methoxy;
—W— is selected from the group consisting of

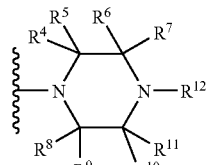

R⁴, R⁵, R⁶, R⁷, R⁸, R⁹, R¹⁰, R¹¹ are each independently H or methyl; with the proviso that not more than two are methyl;

$R^{12}$ is selected from the group consisting of C(O)-phenyl; and

Y is halogen, $OC(O)CH_3$, $OC(O)CF_3$, or other acceptable pharmaceutical salt counterion.

2. The compound of claim 1 wherein:
$R^1$ is methoxy or fluoro; and
$R^4$, $R^5$, $R^6$, $R^7$, $R^8$, $R^9$, $R^{10}$, $R^{11}$ are each H.

3. The compound of claim 2 wherein:
$R^1$ is fluoro; and
Y is Cl.

4. A pharmaceutical composition which comprises an antiviral effective amount of a compound of Formula I, or pharmaceutically acceptable salt(s) thereof, as claimed in any one of claims 1–3, and one or more pharmaceutically acceptable carriers, excipients or diluents.

5. The pharmaceutical composition of claim 4, useful for treating infection by HIV, which additionally comprises an antiviral effective amount of an AIDS treatment agent selected from the group consisting of:

(a) an AIDS antiviral agent;
(b) an anti-infective agent;
(c) an immunomodulator; and
(d) HIV entry inhibitors.

6. A method for treating a mammal infected with the HIV virus comprising administering to said mammal an antiviral effective amount of a compound of Formula I, or pharmaceutically acceptable salt(s) thereof, as claimed in any one of claims 1–3, and one or more pharmaceutically acceptable carriers, excipients or diluents.

7. A method for treating a mammal infected with the HIV virus comprising administering to said mammal an antiviral effective amount of a compound of Formula I, or pharmaceutically acceptable salt(s) thereof, in combination with an antiviral effective amount of an AIDS treatment agent selected from the group consisting of an AIDS antiviral agent; an anti-infective agent; an immunomodulator; and an HIV entry inhibitor.

* * * * *